United States Patent [19]

Chamberlain et al.

[11] 4,372,916
[45] Feb. 8, 1983

[54] ESTABLISHING AND ASCERTAINING DESIRED AIR REMOVAL IN STEAM STERILIZATION

[75] Inventors: Robert E. Chamberlain, Erie; Thomas G. Cook, Fairview, both of Pa.

[73] Assignee: American Sterilizer Company, Erie, Pa.

[21] Appl. No.: 279,209

[22] Filed: Jun. 30, 1981

Related U.S. Application Data

[62] Division of Ser. No. 91,170, Nov. 6, 1979, Pat. No. 4,309,381.

[51] Int. Cl.³ .............................. A61L 2/06; G05B 1/00
[52] U.S. Cl. ......................................... 422/111; 422/3; 422/26; 422/112; 422/116
[58] Field of Search ..................... 422/3, 26, 111, 112, 422/116, 62

[56] References Cited

U.S. PATENT DOCUMENTS

| | | |
|---|---|---|
| 2,112,639 | 3/1938 | Underwood . |
| 2,868,616 | 1/1959 | Poitras . |
| 3,087,210 | 4/1963 | Neiss . |
| 3,402,991 | 9/1968 | Henfrey . |
| 3,409,389 | 11/1968 | Bjork ..................................... 422/26 |
| 3,436,170 | 4/1969 | Lodge ..................................... 422/26 |
| 3,454,352 | 7/1969 | Lamboy et al. ................... 422/26 X |
| 3,479,131 | 11/1969 | Scofheld et al. . |
| 3,494,725 | 2/1970 | Rrons et al. ........................... 422/26 |
| 3,571,563 | 3/1971 | Shutz . |
| 3,967,494 | 7/1976 | Joslyn . |
| 4,115,068 | 9/1978 | Joslyn . |
| 4,164,538 | 8/1979 | Young et al. . |

FOREIGN PATENT DOCUMENTS 2708944 9/1977 Fed. Rep. of Germany ........ 422/26
1143343 2/1969 United Kingdom .

*Primary Examiner*—Barry S. Richman
*Attorney, Agent, or Firm*—Shanley, O'Neil & Baker

[57] ABSTRACT

Air removal is completed and ascertained, in steam sterilization systems which use steam flow through a sterilizing chamber to facilitate air removal, by methods which enable steam-table values for a dependent variable relationship of pressure and temperature, as exhibited by confined saturated steam, to be utilized under steam flow conditions.

Apparatus for controlling and measuring chamber conditions are provided so that such established steam-table values for confined steam can be readily and reliably used to establish and ascertain complete air removal while steam is flowing through the chamber.

In a representative embodiment, chamber pressure is held substantially constant while the remaining variable chamber temperature is measured. Venting of chamber atmosphere is continuous during such control of chamber pressure with chamber temperature being measured until a value is reached corresponding to the steam-table value at the level of the chamber pressure being held.

With complete removal of the air ascertained, sterilizing exposure conditions can be established rapidly by substantially reducing venting of chamber atmosphere since any remaining portions of the cycle, whether establishing or maintaining sterilizing exposure conditions, need not be relied on for removal of air.

Control apparatus, electromechanical and electronic processor, are provided for automatically completing air removal and ascertaining effective air removal.

5 Claims, 8 Drawing Figures

ESTABLISHING AND ASCERTAINING DESIRED AIR REMOVAL IN STEAM STERILIZATION

This is a division of Application Ser. No. 91,170, filed Nov. 6, 1979, now U.S. Pat. No. 4,309,381 issued Jan. 5, 1982, the entire disclosure of which is incorporated herein by reference.

This invention is concerned with steam sterilization in which steam flows through a chamber to facilitate air removal and, more particularly, with processes and apparatus for completing air removal and ascertaining desired removal of air for steam sterilization.

The importance of air removal in steam sterilization processes has been long recognized and emphasized: "—removal of air in steam sterilization is probably the most critical and time consuming portion of a sterilization process—" ("Industrial Sterilization Processes" by Frank E. Halleck, Chapter 25 of Volume 18 of Development in Industrial Microbiology, published by the Society for Industrial Microbiology, 1977).

The need for complete air removal has been further emphasized by governmental regulations such as the Good Manufacturing Practice (GMP) standards for large volume parenteral drug sterilizers of the Federal Drug Administration which require that all air be removed.

Notwithstanding the long history of steam sterilization ("Principles and Method of Sterilization in Health Sciences" by John J. Perkins, Second Edition, Copyright 1969, Charles C. Thomas Publisher) and the emphasis on air removal, commercially acceptable apparatus for evaluating air removal in steam sterilizers has not been evident in the marketplace.

While the invention can be largely defined in terms of finding a practical concept for evaluation of air removal, a significant contribution to commercial practice is the provision of economically and technologically acceptable processes and apparatus for completing air removal and/or ascertaining effective air removal from industrial and hospital sterilizers.

Sterilizers, whether industrial or hospital type, are provided with an access to a steam source. The steam comes to the sterilizer as saturated steam or of high quality but never as superheated steam. The steam flows through the chamber to remove air and heat the load.

While such chambers are sealable, steam sterilization cycles are carried out, for the most part, under steam flow conditions. Steam flow is relied on to facilitate air removal in substantially all steam cycles and in some cycles is relied on entirely for removal of air.

However, an important part of the foundation of the inventive concept is utilization of the properties of a condensable vapor, such as steam, which are exhibited when that vapor is confined in a sealed space and subjected to changing conditions. The pressure and temperature of saturated steam when thus confined exhibit an interdependency which classifies them as dependent variables. Established data on this interdependency of pressure and temperature of saturated steam in a confined space is readily available in steam-tables such as published in "Thermodynamic Properties of Steam" by Keenan and Keys, published by John Wiley and Sons, New York, Copyright 1946. The following are representative data: at atmospheric pressure (14.696 psia), saturated steam exhibits a temperature of 212° F.; at twenty (20) psia, the temperature is 227.96° F.; at twenty-five (25) psia, the temperature is 240.05° F., etc.

In accordance with the invention, methods and apparatus are provided for controlling chamber conditions so that such established steam-table data for confined steam can be used, under the flow conditions found in the chamber, for ascertaining complete air removal. Preferably, the invention completes removal of substantially all air and verifies its removal under steam flow conditions prior to sterilization exposure.

Steam is injected into a sterilizing chamber while provision is made for full venting of chamber atmosphere. In one embodiment, with pressure in the chamber significantly above atmospheric pressure, chamber pressure is controlled while the value within the chamber of the remaining dependent variable, temperature, is measured. Complete air removal is accomplished early in the cycle without relying on thermostatic valves. Steam injection and full venting of chamber atmosphere are carried out with separate control of chamber pressure being exercised and separate measurement of chamber temperature being made until chamber temperature substantially corresponds to the predetermined steam-table value for temperature at the controlled value for chamber pressure.

Processes and apparatus for steam sterilization using steam to facilitate air removal are described more specifically with reference to the accompanying drawings, in which.

Figure 1:
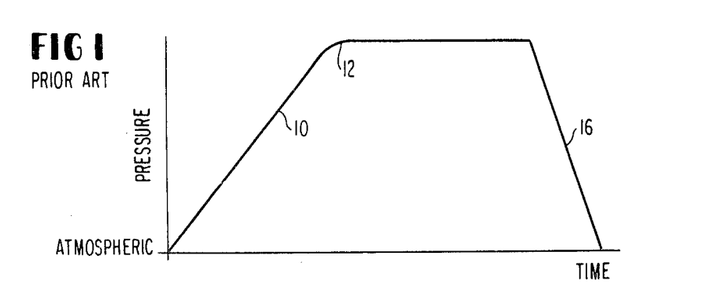
FIG. 1 is a graphical representation of a prior art steam sterilization cycle of the gravity displacement type.

In a typical prior gravity displacement cycle shown graphically in FIG. 1, after loading a sterilizing chamber and closing its access door, steam is injected at or near the top of the chamber. Chamber atmosphere is vented at or near the bottom of the chamber. The heavier air is forced from the chamber by the lighter steam under the influence of gravity.

Chamber pressure increases along line 10 until the selected temperature for sterilization is reached within the chamber at point 12. Then, during sterilization exposure, venting is limited to removal of condensate and remaining air. Steam injection, during sterilization exposure, is limited to that required to maintain sterilization temperature as required for sterilization. In some high temperature cycles, required sterilization exposure is considered to be complete when a preselected high temperature (e.g. 285° F.) is reached and no preselected time interval is provided.

After the required sterilization exposure, the chamber is exhausted along line 16. Drying of the load can also be implemented by applying a vacuum to the chamber.

The chamber door can be opened for removal of goods at atmospheric pressure level.

In accordance with the inventive concept, for sterilization effectiveness, air removal and evaluation of complete air removal are carried out prior to establishment of sterilization exposure conditions under a full venting arrangement for the chamber. A preferred range for control of one of the selected dependent variables is significantly above atmospheric conditions and below the sterilization exposure conditions expected to be used.

Figure 2:
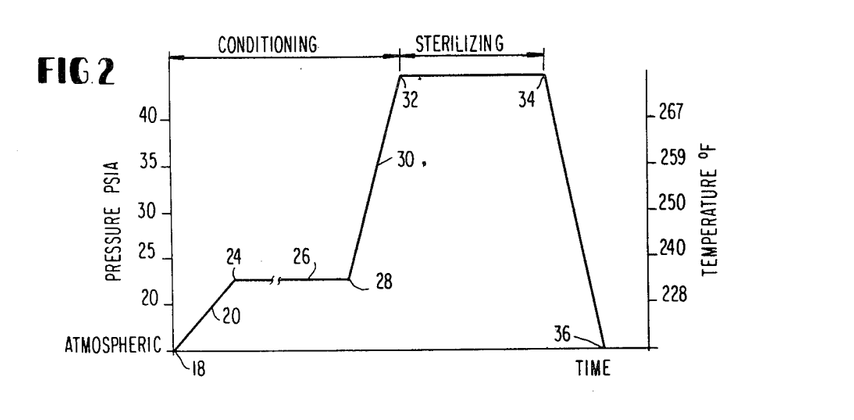
FIG. 2 is a graphical representation of a steam sterilization cycle of the gravity displacement type embodying the invention.

The invention is carried out in this range in the cycle as represented in FIG. 2. At start-up 18, steam is injected with the chamber vented to flush atmosphere from the chamber. Steam injected pressure causes chamber pressure to increase along line 20. At a predetermined value for the selected dependent variable, e.g. between about seventeen point five (17.5) psia and about thirty (30) psia, steam injection is more precisely controlled (starting at point 24) to hold chamber pressure substantially level.

For such control purposes, it is more practical to vary steam injection while maintaining a substantially constant full vent opening. This practice is also preferred so as not to inhibit air removal by reducing venting to achieve the desired level control of the selected dependent variable.

In a representative embodiment of the invention, the chamber value for the selected dependent variable, pressure, is held substantially level at about twenty-one (21) psia along line 26 while chamber temperature is continuously measured or at least measured intermittently.

From established steam-table data, it is known that at about twenty-one (21) psia the value for the remaining dependent variable, temperature, should be approximately 230° F. (more precisely 230.57° F.). The initial chamber temperature measurements, at point 24 in FIG. 2, with air in the chamber, will have a value less than 230° F. With chamber venting continuing and steam injection controlled, chamber pressure is held substantially level. Chamber temperature will increase as air is removed. At point 28, when chamber temperature reaches 230° F. under the chamber control condition imposed, substantially all air has been removed. Then steam injection is increased to rapidly increase pressure along line 30. Also, at point 28, as a result of the invention, sterilization exposure conditions can safely be established more rapidly by substantially diminishing chamber venting; in fact, for air removal purposes, chamber venting can be eliminated since all air has been removed.

The above evaluation can be carried out, or reverified, at any point along the line 30. When this evaluation is carried out at a pressure substantially corresponding to desired sterilization temperature, the required sterilization exposure can be implemented directly upon completion of the verification of air removal.

In the cycle illustrated in FIG. 2, sterilization exposure time extends between points 32 and 34. Thereafter, the chamber is exhausted to atmospheric pressure at point 36.

When temperature is the selected dependent variable, a chamber temperature is preferably selected above 220° F. and below sterilization exposure temperature. Chamber temperature is held substantially level at the selected value, e.g. 230° F., by controlled steam injection with full venting as chamber pressure is measured.

Figure 3:
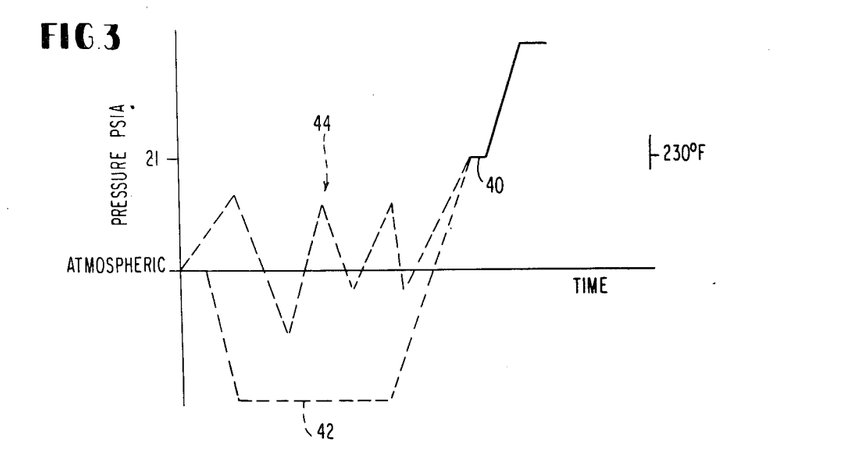
FIG. 3 is a graphical representation of other types of steam sterilization cycles embodying the invention.

Under these circumstances, line 44 of FIG. 3 can be used to represent temperature by referring to the temperature scale on the right side of the graph.

As the selected temperature 230° F. is first reached and chamber pressure is measured, chamber pressure, because of the partial pressure of air, will have a value greater then twenty-one (21) psia. With continued steam injection and full venting of the chamber atmosphere, chamber pressure diminishes as chamber temperature is held constant. As chamber pressure reaches twenty-one (21) psia, substantially all air has been removed. The required exposure to complete sterilization can then take place as previously described.

Specific chamber control procedures other than holding chamber value for one dependent variable substantially constant can be utilized while still achieving the interrelation required when chamber conditions are measured. For example, steam can be injected until a preselected temperature, e.g. 230° F., is reached. Chamber pressure is measured, steam injection is interrupted, and venting continues. With air in the chamber, the initially measured chamber pressure will be greater than twenty-one (21). With the vent opening, both chamber temperature and pressure will diminish until a preselected value is reached; then, steam injection is reinitiated to raise the chamber to the initially selected temperature. Pressure and temperature will vary under this procedure as air is forced from the chamber. When chamber pressure, at the selected temperature value, corresponds to established steam-table data, all air has been removed.

Air removal and verification can also be carried out by preselecting a pressure, interrupting steam injection, measuring temperature, and allowing the chamber pressure and temperature to vary under the above procedure until the established steam-table values are reached at the preselected pressure.

FIG. 3 represents application of the invention to a sterilization cycle using vacuum as part of the conditioning. The air removal evaluation is shown as made at the levels discussed in relation to the gravity displacement cycle of FIG. 2. For example, in FIG. 3, the above described air removal determination is shown being carried out along line 40, at about twenty-one (21) psia and 230° F. The use of a high vacuum for an extended interval is shown by broken line 42; a cyclic pulsing approach is shown generally by broken line 44. With cyclic pulsing, the air removal evaluation can be applied during pulsing. If completion of air removal is verified in a particular pulse, required sterilization exposure can begin; otherwise, the pulsing can continue until effective air removal is ascertained.

Figure 4:
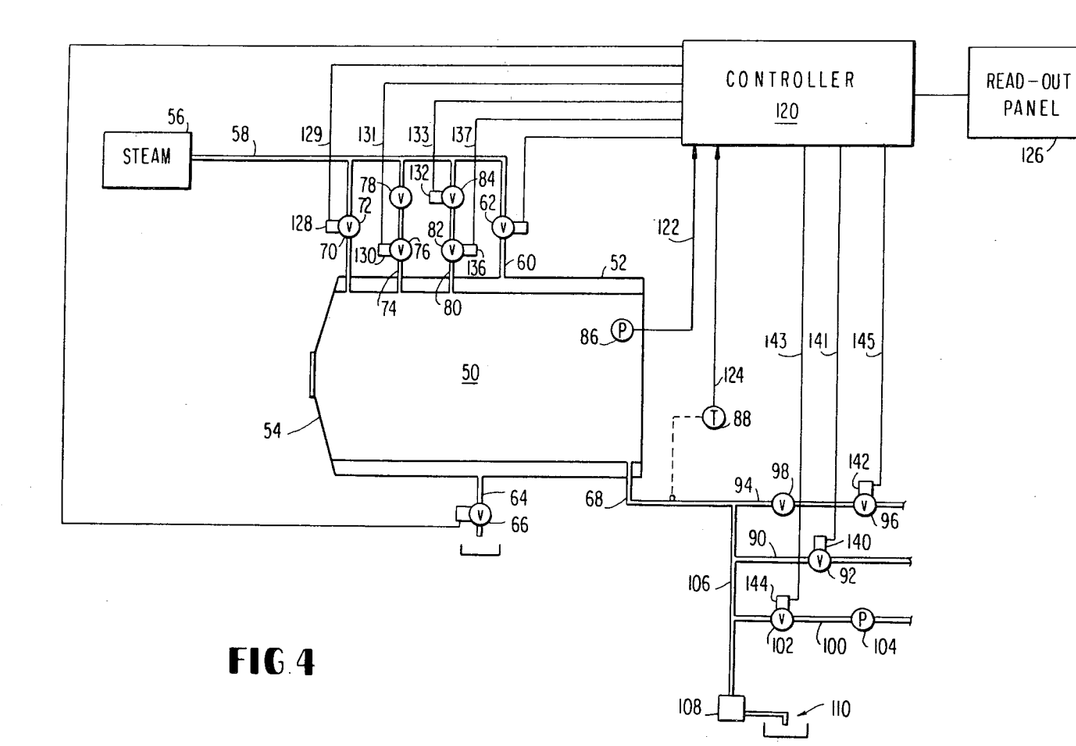
FIG. 4 is a schematic illustration of steam sterilization apparatus embodying the invention.

Apparatus which can be used for gravity displacement and/or vacuum augmented air removal cycles is shown in composite form in the schematic of FIG. 4. A chamber 50, capable of operating at other than atmospheric pressure, is surrounded by an insulating jacket 52 and includes an access door 54. Steam from a source 56 is provided through conduit 58 generally at a pressure between about fifty (50) and eighty (80) psia. Jacket steam is delivered through conduit 60 under the control of valve 62 and the jacket is drained through conduit 64 through valve 66. Conventional methods and means for selecting and maintaining a jacket temperature can be used.

Chamber atmosphere is removed through chamber drain 68. The chamber control providing for use of steam-table data is achieved in the illustrated embodiment through use of multiple steam inlets and multiple chamber atmosphere vents.

Main steam inlet conduit 70 provides a high rate of steam flow for flushing air from the chamber and bringing the chamber up to sterilizing conditions. Valve 72 controls flow in conduit 70.

In contrast to such main steam inlet conduit, steam inlet conduit 74 provides for a lower rate of steam flow. This lower rate facilitates more precise control of chamber conditions; e.g. holding a chamber pressure level. Valve 76 provides on/off control. Throttle control valve 78 is also provided in conduit 74 and can be used to isolate conduit 74.

Conduit 80 provides an alternate steam inlet path for precise control of chamber conditions. In such an alternate, valve 82 is pressure regulating. Conduit 80 includes on/off valve 84 for purposes of excluding conduit 80 when steam inlet conduit 74 is being used.

Sensing chamber pressure and temperature and providing signals or responses indicative of such chamber conditions are important in practice of the invention. Chamber pressure sensing means 86 are located within the chamber. Chamber temperature sensing means 88 are shown located within drain line 68 but can be otherwise located in the chamber. Multiple sensing devices or measurements are likely to be used in most control systems; the sensing means designations are therefore inclusive, i.e. pressure sensing means 86 may comprise pressure (actuated) switches and/or pressure sensors with signal generating means (pressure transducers) and, temperature sensing means 88 may comprise temperature switches and/or temperature transducers.

The plurality of conduits for coordinating and controlling removal of chamber atmosphere include a main vent conduit 90, with vent valve 92 for high volume venting during air flush charging of steam or exhausting the chamber to atmospheric pressure.

A diminished removal flow can be provided through conduit 94 which includes "constant-bleed" valve 96 and throttle valve 98.

Evacuation conduit 100 with valve 102 and pump (or ejector) means 104 are provided for cycles using vacuum for conditioning, exhausting the chamber or drying the load.

Conduit 106 includes a cooling portion leading to a trap. Thermostatic valve 108 with trap 110 can be utilized. Thermostatic valves automatically remove condensate or air accumulating in a cooling conduit located so as to contact a thermally responsive element. Thermostatic valves have been used in the past for removing cooled condensate and air, especially during the sterilization exposure phase notwithstanding their questionable long-term reliability (see Perkins text identified above).

Verification that all air has been removed under full venting conditions as taught by the invention was not available in any known prior practice. Use of a thermostatic valve for air removal during the "charging" phase would unduly extend cycle times. The likely solution to improper air removal in other types of practice would have been to rely on a thermostatic valve for air removal during sterilization exposure times.

In the apparatus of FIG. 4, electrical solenoids, which are remotely and automatically controllable, provide the means for coordinated control of steam inlet and chamber atmosphere removal conduits. Controller 120 can be relied on for selection of values, timing and coordinating control; pressure and temperature switches set at preselected values can be relied on for selection of some values as described later. Chamber pressure signals are directed from the pressure sensing means 86 to controller 120 over line 122; and temperature signals from sensor 88 are directed over line 124. Display of selected or actual chamber values, as well as indication of complete air removal, can be presented at read-out panel 126.

Referring to the steam inlet side of the chamber for nomenclature, the high volume "come-up" or flushing valve 72 is controlled by solenoid 128 through line 129 to controller 120; valve 76 is controlled by solenoid 130 through line 131; on/off valve 84 in pressure regulating conduit 80 is controlled by solenoid 132 through line 133, and the regulated pressure established by valve 82 is established by pressure selector 136 through line 137 to controller 120.

Referring to the chamber atmosphere removal structure, solenoid 140 controls main vent valve 92 through line 141 to controller 120; solenoid 142 controls valve 96 through line 145, and solenoid 144 controls valve 102 through line 143.

With temperature sensing means 88 located in drain line 68, constant-bleed valve 96 remains open during the sterilization phase in order to assure, by movement of chamber atmosphere through the drain line 68, that the temperature measured in the drain line is substantially the same as chamber temperature and drain line temperature is assured throughout the chamber by locating the temperature sensor in the drain line.

Referring to the gravity cycle graph of FIG. 2 illustrating use of the invention, at the start of the cycle main steam inlet valve 72 and main vent valve 92 are opened. Steam under pressure flows into the chamber as chamber atmosphere is being removed such that chamber pressure builds along line 20 because of the relative size of the main steam inlet valve and main chamber vent valve. The main inlet valve 72 and the main vent valve 92 remain open during flushing along line 20. The main vent valve remains open at other times; e.g. when the air removal evaluation is being made along line 26.

Some control of the selected dependent variable, e.g. pressure along line 26 of FIG. 2, could be exercised by on/off control of main valve 72. However, more precise control facilitating the type of measurements to be made for most effective use of the invention is provided through inlet conduit 74 or inlet conduit 80.

With the pressure being held substantially level (about 21 psia), chamber temperature is being measured by temperature sensor 88. When chamber temperature reaches the level corresponding to the pressure being held, substantially all air has been removed and air removal has been verified.

Figure 5:
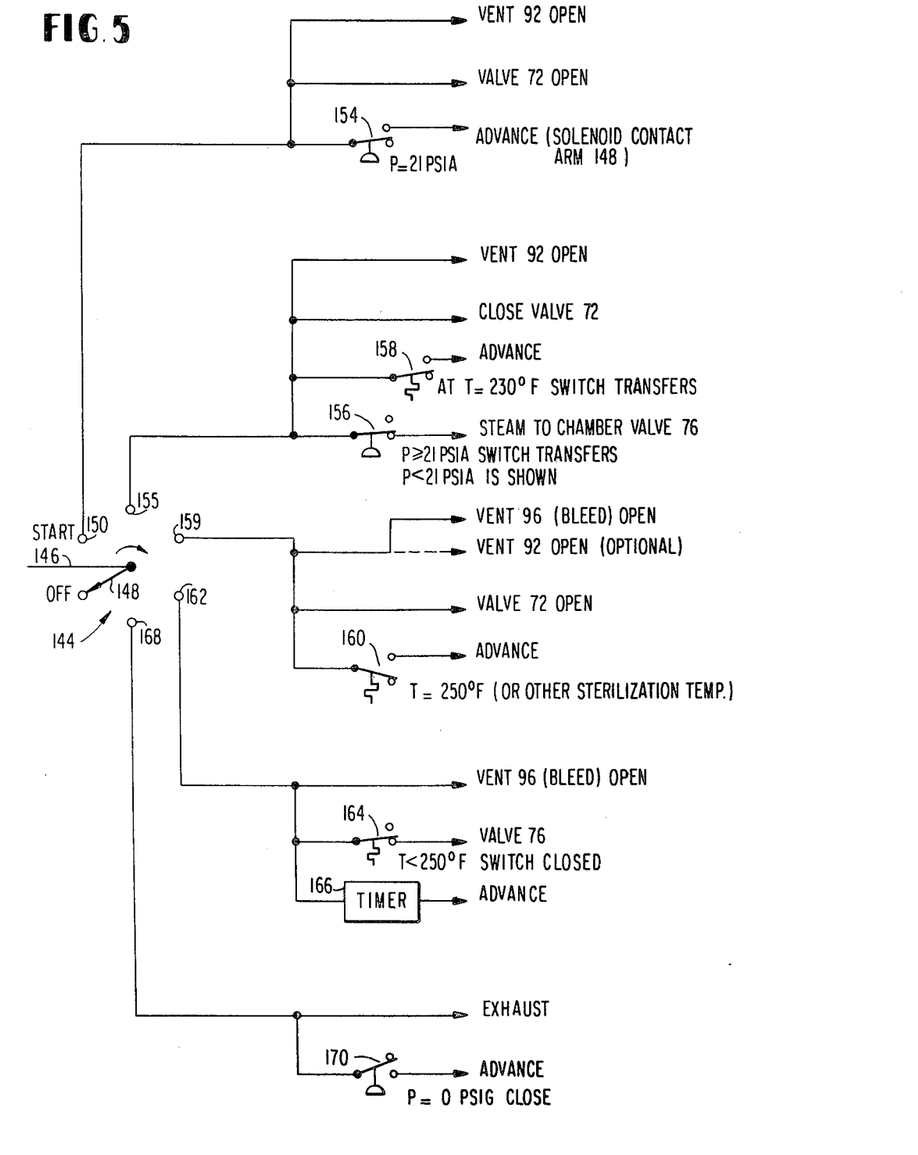
FIG. 5 is a schematic circuit diagram of electromechanical type control apparatus embodying the invention.

The circuit schematic of FIG. 5 presents electromechanical apparatus to control operation between start-up of the cycle at point 18 (FIG. 2) through completion at point 36 and is presented in terms of a cycle in which chamber conditions are controlled to hold chamber pressure substantially level while chamber temperature is measured. Rotary type solenoid 144 comprises a rotary stepping or switching device. An electrical "advance" signal on line 146 causes switching arm 148 to sequentially advance to various contact positions on the solenoid.

At start-up, switching arm 148 closes the circuit through contact 150. The main steam inlet valve 72 and the main chamber atmosphere vent valve 92 are opened. Pressure builds along line 20 (FIG. 2) as chamber atmosphere is flushed from the chamber by the pressurized steam.

When pressure reaches the selected level 21 psia, pressure switch 154 is actuated causing an "advance" signal to the rotary solenoid switching contact arm 148 to contact position 155. The air removal and evaluation portion of the cycle, as illustrated between points 24 and 28 of FIG. 2, is carried out at this location of the contact arm.

The main chamber atmosphere vent valve 92 remains open and main steam valve 72 is closed. Valve 76 in the control conduit 74 is controlled by pressure switch 156 to hold the pressure in the chamber at the selected level of twenty-one (21) psia.

Temperature is being measured by the temperature responsive element of temperature switch 158. When 230° F. is reached, the temperature switch changes state sending an advance signal to input line 146 of rotary solenoid 144. Contact arm 148 is switched to contact position 159.

In position 159, the chamber is raised to sterilization exposure conditions along line 30 of FIG. 2 between points 28 and 32. The flow rate of steam into the chamber is increased by opening the main steam inlet valve 72. While full venting of the chamber atmosphere can, optionally, be continued through the main vent 92, this is not necessary because substantially all air has been removed. The use of reduced venting is preferred.

An advantage of the present invention is that further venting for air removal purposes is not required after air removal has been verified. This contrasts with prior practice of gravity displacement cycles in which air flushing was required throughout the charging phase and in which it was required to depend on satisfactory operation of a thermostatic valve during the exposure phase for air removal purposes. While a continuous bleed venting through conduit 94 may be required, steam loss to the environment is reduced and the come-up time along line 30 is reduced. The bleeder vent valve 96 would be required to maintain accuracy of chamber temperature measurement when the temperature sensor is in the drain line.

When the temperature sensing element of temperature switch 160 reaches the selected sterilization temperature, e.g. 250° F., the temperature switch causes an advance signal to be sent to the rotary solenoid 144 switching the solenoid arm 158 to position 162.

With the rotary solenoid switching arm 148 in position 162, desired sterilization exposure is carried out along line 32–34 of FIG. 2; that is, the chamber temperature is held at the selected level for the desired sterilization interval. Constant bleeder valve 96 is opened or remains open for the purposes mentioned. Steam injection through valve 76 is controlled by temperature switch 164 to hold the temperature at 250° F. Timer 166 is also initiated as arm 148 switches to contact position 162 and, at the expiration of the selected time, timer 166 causes an advance signal to be sent to the rotary solenoid 144 switching relay arm 148 to contact position 168.

An exhaust phase, dependent on the cycle and the materials in the sterilizer load, is then carried out with the option of various modes well known in the art. Upon the completion of the exhaust phase, when pressure reaches atmospheric level (zero psig, 14.7 psia), switch 170 closes advancing the solenoid to the "off" position terminating the cycle.

If the air removal evaluation is to be carried out by other methods as described earlier, such as holding the chamber temperature substantially level while measuring pressure, appropriate control apparatus is substituted at the contact 155. For example, when temperature is the selected dependent variable, a temperature switch is used to hold chamber temperature at the selected level (230° F.) and a pressure switch actuates the advance when the chamber pressure comes down to the established value (21 psia).

Figure 6:
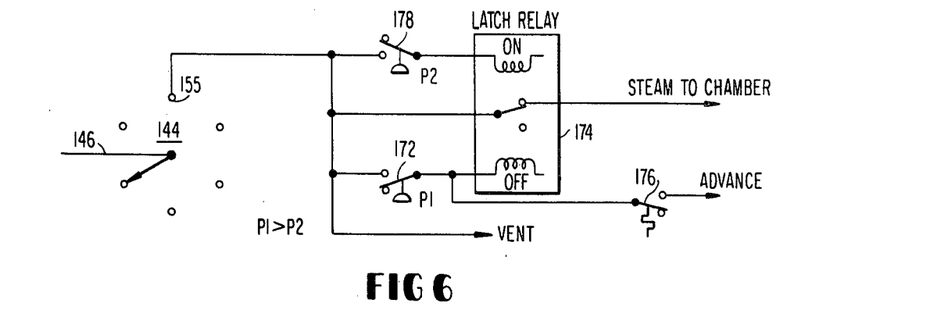
FIG. 6 is a schematic circuit diagram of control apparatus which may be substituted for a portion of FIG. 5.

As a further example, FIG. 6 schematically illustrates apparatus for air removal and evaluation when the selected dependent variable is controlled by being allowed to vary between two levels rather than being held substantially constant as in the preferred embodiment. The circuit of FIG. 6 is connected to contact 155 in place of that shown in FIG. 5. When the pressure in the chamber reaches a selected level $P_1$ (e.g. 21 psia), pressure switch 172 through latch relay 174 cuts off main steam valve 72 to the chamber. With air in the chamber, temperature switch 176 will not change state since chamber temperature will be below the established steam-table value of 230° F.

Main vent 92 remains open with the main inlet valve 72 closed so that chamber temperature and pressure drop until a preselected pressure $P_2$ is reached. Pressure switch 178, when $P_2$ is reached, changes state from that shown to send steam of the chamber (valve 72 or 76 can be utilized) to raise chamber pressure and temperature. This type of oscillation continues until the established steam-table value for the temperature (230° F.) is reached at $P_1$ (21 psia, both pressure switch 172 and temperature switch 176 in a changed state from that shown), thus completing air removal and evaluation. Under such circumstances, temperature switch 176 advances the contact arm of rotary solenoid 44 to continue the cycle.

Electronic processor apparatus can also be used with some advantages over electromechanical apparatus. For example, with a large computer memory, data on a desired range of the entire graphical relationship between the dependent variables can be readily stored and the level for the air removal and evaluation operations readily selected to take place along the stored portion of the graph. When using an electronic processor, pressure transducers and temperature transducers can be substituted for pressure switches and temperature switches, respectively. For example, thermocouples and resistance temperature detectors (RTDs) can be used in place of temperature switches. Also, ease of selection of parameter values for a particular cycle is facilitated with electronic processor equipment over that available with electromechanical equipment. Further, reverification of air removal at any point in the cycle is more easily obtained by resorting to the memory of the electronic processor.

Figure 7:
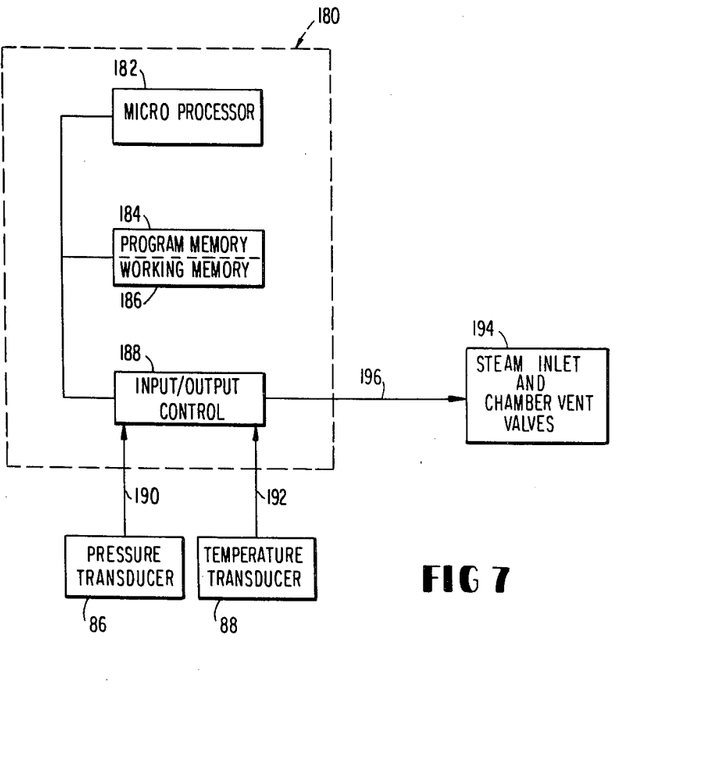
FIG. 7 is a schematic box diagram of electronic processor control apparatus embodying the invention.

In the electronic processor apparatus of FIG. 7, controller 180 includes microprocessor 182, program memory 184, working memory 186, and input/output control 188. Pressure and temperature signals from pressure transducer 86 and temperature transducer 88 are transferred on lines 190 and 192 to the input/output control for comparison with steam-table stored values. Signals to the various valves for steam inlet and chamber atmosphere venting, represented by box 194, are transferred over line 196.

Figure 8:
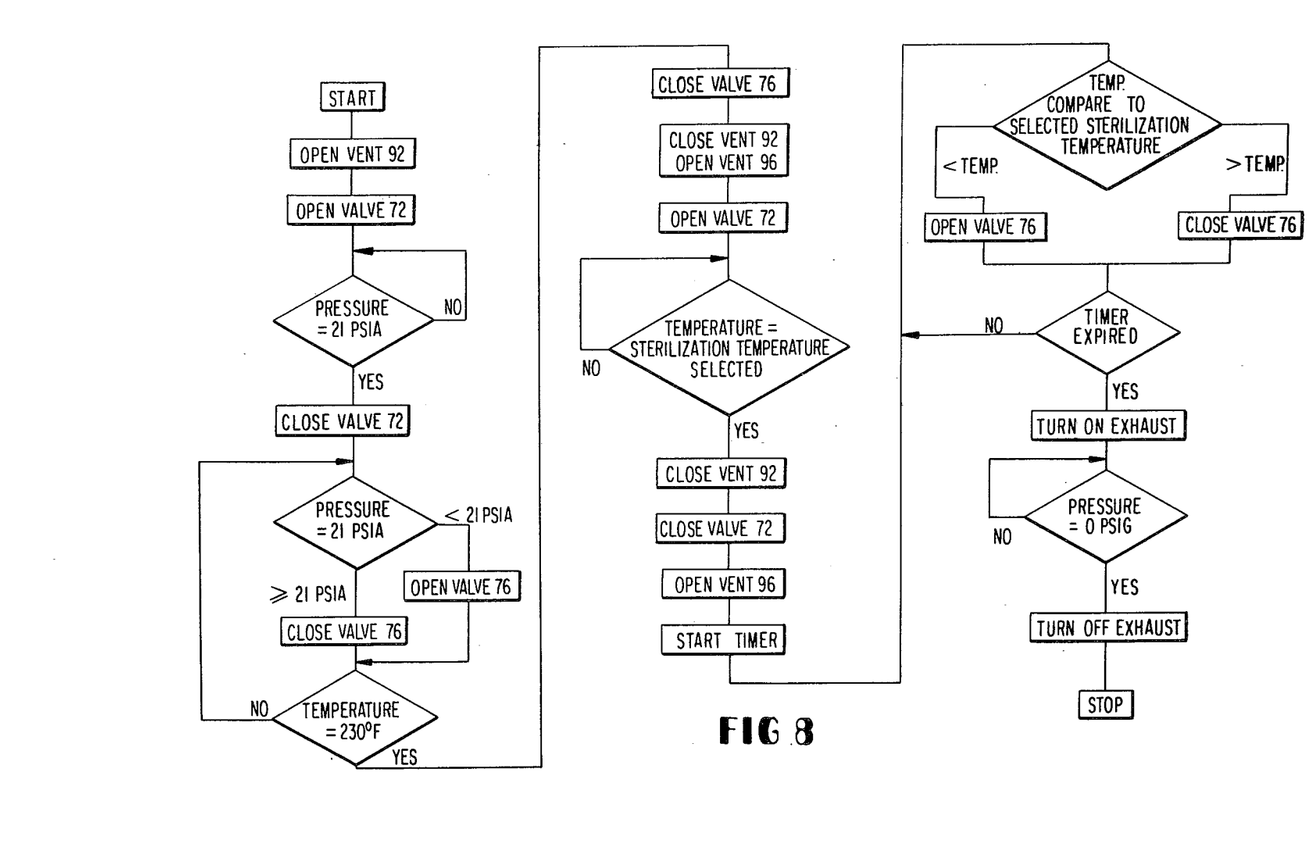
FIG. 8 is a flow chart for electronic processor control apparatus embodying the invention.

The flow chart of FIG. 8 relates to a gravity displacement cycle but can be readily modified by those skilled in the art for cycles which use a vacuum to augment air removal based on the disclosure presented earlier. In FIG. 8, pressure is the preselected dependent variable to be held substantially constant at about twenty-one (21) psia while chamber temperature is measured until air removal is completed and such air removal ascertained. As shown in the flow chart, at start-up the main chamber atmosphere vent 92 and the main come-up steam inlet valve 72 are opened. Pressure increases until chamber pressure of twenty-one (21) psia is signaled by pressure transducer 86.

When the preselected pressure is reached, chamber pressure is held substantially level through reduced flow of steam. Valve 76 facilitates this control while the main steam inlet valve 72 is closed. Chamber temperature is measured until a value of approximately 230° F. is read.

When chamber temperature reaches 230° F., substantially all air has been removed from the chamber and the chamber can be brought up to sterilizing exposure conditions. Since substantially all air has been removed, the high rate of venting from the chamber to flush chamber atmosphere need no longer be continued and venting can be substantially reduced. Main steam inlet valve 72 is opened and main vent 92 is preferably closed during the come-up period while constant bleed vent 96 is opened or remains open. The bleeder valve remains open in this embodiment for the purpose stated, i.e. to help maintain the accuracy of the chamber temperature reading obtained from a temperature sensor in the drain line.

At sterilizing temperature, the main steam inlet valve 72 is closed; the constant bleed valve 96 is maintained open and main vent 92 is maintained closed as the timer is started.

The selected sterilization temperature is maintained by control of chamber steam inlet valve 76. After expiration of the required exposure time, exhaust is started with steam inlet valves closed. Upon completion of the exhaust, when the pressure substantially equals atmospheric pressure, the exhaust is stopped and the cycle terminates.

The individual electrical elements and devices identified in relation to FIGS. 4, 5, 6 and 7, as well as equivalent devices, are readily available commercially and their individual operations are well known in the art. It is their combination in accordance with the present teachings which provides the unique aspects of the invention. In presenting representative embodiments, specific process steps and apparatus have been described; however, modifications or substitutions can be made which fall within the scope of the invention. Therefore, in evaluating the scope of this invention, reference should be made to the appended claims.

We claim:

1. Apparatus for steam sterilization of goods utilizing steam flow through a chamber to facilitate removal of air during a load conditioning phase and providing for determination of effective air removal by correlating measured chamber conditions with steam-table established data for the dependent variables of pressure and temperature for saturated steam, comprising
   a sterilizing chamber capable of operating at pressures above atmospheric,
   steam inlet conduit means including automatically controllable valve means,
   chamber atmosphere vent conduit means including automatically controllable vent valve means having a substantially wide open configuration and a substantially closed configuration,
   chamber pressure sensing means,
   chamber temperature sensing means,
   means providing for use of predetermined steam-table values for the dependent variables of pressure and temperature for saturated steam,
   controller means for controlling injection of steam into the chamber and venting of chamber atmosphere from the chamber to hold one of such variables substantially level while measuring the remaining of such variables,
   such controller means being responsive to such chamber pressure sensing means, such chamber temperature sensing means and such means providing for use of predetermined steam-table values to ensure that substantially all air has been removed during the load conditioning phase,
   such chamber venting being carried out with such vent valve means in such substantially wide open configuration during air removal from the chamber followed by rapidly pressurizing the chamber,
   such chamber vent valve means being in its substantially closed configuration for carrying out a sterilization exposure phase, with such sterilization phase being followed by an exhaust phase which returns chamber pressure to substantially atmospheric pressure level.

2. The apparatus of claim 1 in which
   the chamber pressure sensing means includes
   pressure transducer means interconnected with the controller means,
   the chamber temperature sensing means includes
   temperature transducer means interconnected with the controller means, and
   such means providing for use of predetermined steam-table values includes
   means for storing steam-table established values for the dependent variables of pressure and temperature for saturated steam, and
   such controller means includes
   means for comparing chamber sensed pressure and temperature values with such stored steam-table values of pressure and temperature for saturated steam.

3. The apparatus of claim 1 in which the steam inlet conduit means including automatically controllable valve means provides for selection of differing flow rates of steam injection and comprises
   on/off valve means providing a selected rate of steam injection which facilitates bringing a load up to desired temperature during the conditioning phase, and
   on/off valve means providing a lower rate of steam injection for maintaining desired load temperature during the sterilization phase.

4. The apparatus of claim 1 in which
   the chamber pressure sensing means includes pressure switch means operative at a preselected chamber pressure to hold chamber pressure at a preselected pressure level during such conditioning phase.

5. The apparatus of claim 4 in which
   the chamber temperature sensing means includes temperature switch means operative, while chamber pressure is being held at such preselected level by the pressure switch means, to change state when the chamber temperature corresponding to the steam-table temperature value at such preselected chamber pressure level is reached.

* * * * *